(12) United States Patent
Traeger et al.

(10) Patent No.: US 12,257,316 B2
(45) Date of Patent: Mar. 25, 2025

(54) NANOSTRUCTURED ACTIVE INGREDIENT CARRIER SYSTEM

(71) Applicant: Friedrich-Schiller-Universitaet Jena, Jena (DE)

(72) Inventors: Anja Traeger, Trebgast (DE); Anne-Kristin Truetzschler, Jena (DE); Tanja Bus, Jena (DE); Ulrich Sigmar Schubert, Jena (DE)

(73) Assignee: FRIEDRICH-SCHILLER-UNIVERSITAET JENA, Jena (DE)

( * ) Notice: Subject to any disclaimer, the term of this patent is extended or adjusted under 35 U.S.C. 154(b) by 100 days.

(21) Appl. No.: 17/810,511

(22) Filed: Jul. 1, 2022

(65) Prior Publication Data

US 2022/0401577 A1    Dec. 22, 2022

Related U.S. Application Data

(63) Continuation of application No. 16/476,752, filed as application No. PCT/DE2018/100012 on Jan. 10, 2018, now Pat. No. 11,376,336.

(30) Foreign Application Priority Data

Jan. 10, 2017    (DE) ...................... 10 2017 100 317.7

(51) Int. Cl.
| | | |
|---|---|---|
| *A61K 9/51* | (2006.01) | |
| *A61K 47/54* | (2017.01) | |
| *A61K 47/58* | (2017.01) | |
| *A61K 47/69* | (2017.01) | |

(52) U.S. Cl.
    CPC ........ *A61K 47/6933* (2017.08); *A61K 9/5153* (2013.01); *A61K 47/58* (2017.08)

(58) Field of Classification Search
    None
    See application file for complete search history.

(56) References Cited

U.S. PATENT DOCUMENTS

| | | | |
|---|---|---|---|
| 9,795,688 B2 | 10/2017 | Bauer | |
| 11,376,336 B2* | 7/2022 | Traeger | ............... A61K 9/5153 |
| 2004/0042972 A1 | 3/2004 | Truong | |
| 2016/0220697 A1* | 8/2016 | Bauer | .................... A61P 43/00 |
| 2016/0243048 A1 | 8/2016 | Xu | |

FOREIGN PATENT DOCUMENTS

| | | | |
|---|---|---|---|
| DE | 102007059752 A1 | 6/2009 | |
| EP | 2522689 A1 | 11/2012 | |
| EP | 2848262 A1 | 3/2015 | |
| WO | 2012156058 A1 | 11/2012 | |
| WO | WO-2015035974 A1 * | 3/2015 | .......... A61K 31/713 |
| WO | 2015058111 A1 | 4/2015 | |

OTHER PUBLICATIONS

Rinkenauer Alexandra C et al: "Comparison of the uptake of methacrylate-based nanoparticles in static and dynamicin vitrosystems as well asin vivo" Journal of Controlled Release. vol. 216. Aug. 12, 2015 (Aug. 12, 2015), pp. 158-168.

Nicole Ali McNeer et al: "Nanoparticles that deliver triplex-forming peptide nucleic acid molecules correct F508del CFTR in airway epithelium". Nature Communications. vol. 6. Apr. 27, 2015.

Schallon: "Performance of three PDMAEMA-based polycation architectures as gene delivery agents in comparison to linear and branched PEI". Reactive & Functional Polymers. vol 70. No. 1. Jan. 1, 2010 (Jan. 1, 2010). p. 1.

Biswas, S.; Deshpande, P. P.; Navarro, G.; Dodwadkar, N. S.; Torchilin, V. P., Lipid modified triblock PAMAM-based nanocarriers for siRNA drug co-20 delivery. Biomaterials 2013, 34 (4), 1289-1301.

Rinkenauer, A. C.; Schallon, A.; Guenther, U.; Wagner, M.; Betthausen, E.; Schubert, U.S.; Schacher, F. H., A Paradigm Change: Efficient Transfection of Human Leukemia Cells by Stimuli-Responsive Multicompartment Micelles. ACS Nano 2013, 7 (II), 9621-9631.

Osawa, S.; Osada, K.; Hiki, S.; Dirisala, A.; Ishil, T.; Kataoka, K., Polyplex Micelles with Double-Protective Compartments of Hydrophilic Shell and Thermoswitchable Palisade of Poly(oxazoline)-Based Block Copolymers for Promoted Gene Transfection. Biomacromolecules 2016, 17 (1), 354-361.

Feng, G.; Chen, H.; Li, J.; Huang, Q.; Gupte, M. J.; Liu, H.; Song, Y.; Ge, Z., Gene therapy for nucleus pulposus regeneration by heme oxygenase-! plasmid DNA carried by mixed polyplex micelles with thermo-responsive heterogeneous coronas. Biomaterials 2015, 52, 1-13.

A nonviral pHEMA+chitosan nanosphere-mediated high-efficiency gene delivery system, Eroglu, Erdal; Tiwari, Pooja M.; Waffo, Alain B.; Miller, Michael E.; Vig, vol. 2013:8(1) pp. 1403-1415 DOI https://dx.doi.org/10.2147/IJN.S43168.

(Continued)

*Primary Examiner* — Brian Gulledge
(74) *Attorney, Agent, or Firm* — Abel Schillinger, LLP

(57) ABSTRACT

The invention relates to a nanostructured active ingredient carrier system, in particular for reducing cytotoxic properties owing to the use of sheath polymer and the transport resulting therefrom, for interactions with cell membranes during the transport of hydrophilic constituents and, in connection therewith, the generation of an early endosomal release of the interaction complex from the carrier system. The problem addressed by the present invention is that of specifying a nanostructured active ingredient carrier system which avoids the disadvantages of the prior art and in particular permits a reduction in cytotoxic properties owing to the use of a sheath polymer and the transport resulting therefrom. This problem is solved in that a nanostructured active ingredient carrier system is provided in the form of a particle consisting of a carrier sheath, wherein the carrier sheath comprises at least one or more hydrophobic sheath polymers, one or more charged complexing polymers and one or more hydrophilic active ingredients, wherein the complexing polymer interacts with the active ingredient.

16 Claims, 11 Drawing Sheets

(56) References Cited

OTHER PUBLICATIONS

Ko, Y. T.; Bickel, U., Liposome-Encapsulated Polyethylenimine/ Oligonucleotide Polyplexes Prepared by Reverse-Phase Evaporation Technique. Pharm. Sci. Tech 2012, 13 (2), 373-378.
Ge, X.; Duan, S.; Wu, F.; Feng, J.; Zhu, H.; Jin, T., Polywraplex, Functionalized Polyplexes by Post-Polyplexing Assembly of a Rationally Designed Triblock Copolymer Membrane. Adv. Funct. Mater. 2015, 25 (27), 4352-4363).
Choi, K.-m.; Jang, M.; Kim, J. H.; Ahn, H. J., Tumor-specific delivery of siRNA using supramolecular assembly of hyaluronic acid nanoparticles and 2b RNA-binding protein/SIRNA complexes. Biomaterials 2014, 35 (25), 7121-7132.
International Search Report dated Mar. 22, 2018 with regard to International Application No. PCT/DE2018/100012.
Bayo-Puxan et al., J. Control, Release, 2011, vol. 156, pp. 118-127. (Year: 2011).

\* cited by examiner

| Polymer | Mn(A) [g mol⁻¹] | Đ | DP(B) DMAEMA | DP(B) BocMAEMA | DP(b) BocAEMA |
|---|---|---|---|---|---|
| P2 | 35600 | 1.08 | - | 146 | - |
| P3 | 33800 | 1.10 | - | - | 146 |
| P4 | 34400 | 1.16 | 101 | 68 | - |
| P5 | 49800 | 1.19 | 116 | - | 86 |
| P6 | 54600 | 1.14 | - | 115 | 115 |
| P7 | 46200 | 1.25 | 73 | 73 | 73 |

| Polymer | Mn(AF4) | Ð(AF4) | Mn(SEC) | Ð(SEC) | DP | pK |
|---------|---------|--------|---------|--------|-----|------|
| P1[c]   | 26200   | 1.09   | 29000   | 1.09   | 185 |      |
| P2      | 24000   | 1.21   | 13400   | 2.04   | 167 | 7.01 |
| P3      | 21400   | 1.10   | 11700   | 1.98   | 163 | 7.71 |
| P4      | 31500   | 1.14   | 17900   | 2.15   | 208 | 7.48 |
| P5      | 37000   | 1.12   | 16500   | 2.19   | 249 | 6.90 |
| P6      | 46000   | 1.28   | 20000   | 2.26   | 348 | 7.22 |
| P7      | 36000   | 1.27   | 21800   | 2.35   | 250 | 7.57 |

NANOSTRUCTURED ACTIVE INGREDIENT CARRIER SYSTEM

CROSS-REFERENCE TO RELATED APPLICATION(S)

This application is a continuation of U.S. application Ser. No. 16/476,752, filed Jul. 9, 2019, entitled "NANOSTRUCTURED ACTIVE INGREDIENT CARRIER SYSTEM," naming inventors Anja TRAEGER, Anne-Kristin TRUETZSCHLER, Tanja BUS, and Ulrich Sigmar SCHUBERT, which is a national stage entry under 35 U.S.C. § 371 of International Application No. PCT/DE2018/100012, filed Jan. 10, 2018, which claims priority to German Patent Application No. 102017100317.7 filed Jan. 10, 2017, all of which are assigned to the current assignee hereof and incorporated herein by reference in their entireties.

FIELD OF THE DISCLOSURE

The invention relates to a nanostructured active ingredient carrier system, in particular for reducing cytotoxic properties due to transport, for interacting with cell membranes during transport of hydrophilic components and, associated therewith, for generating early endosomal release of the interaction complex from the carrier system.

BACKGROUND

According to the prior art, the use of polymers for encapsulation, for the complexation of nanostructures and/or for the encapsulation of nucleic acids for therapeutic purposes as well as in basic research is already known. This includes above all the field of combined cancer therapy with additional active ingredient delivery and the delivery of genetic material for protein regulation in the cell tissue.

The delivery of the nucleic acids can be subdivided into the following areas:
  i) The complexation of nucleic acids by means of electrostatic interactions and
  ii) the inclusion of nucleic acids in a hydrophobic polymeric system.

With regard to the complexation of the nucleic acids by means of electrostatic interactions, the following technical solutions should be mentioned, for example:

WO 2015058111 A1 discloses a nanoparticle in which a hydrophobic active ingredient as well as nucleic acids, preferably siRNA, are enclosed by the interaction with hydrophobic and/or cationic-hydrophilic shell polymers. This formulation is used for a controlled release of the active ingredients and for the protection of the nucleic acids.

The disadvantage of this technical solution is that cationic-hydrophobic substances and amphiphilic polymers are used. The further disadvantage of this technical solution is that, due to the use of polyethylene glycol, the corona used can already possibly lead to an immune response to organisms containing antibodies.

In addition, the application as an anticarcinogenic therapeutic agent is intended and beneficial for a longer release of the active ingredient, and yet the moderately cytotoxic polyethylenimine is used. The structure of the system with more than 2 different types of polymers also makes it difficult to produce the nanoparticles.

The prior art also discloses the formulation of micellar polymer nanotubes with a complexation of nucleic acids on the outer corona.

A block which has cationic charges undergoes electrostatic binding to the genetic material (Biswas, S., Deshpande, P P, Navarro, G.; Dodwadkar, N S, Torchilin, V P, Lipid modified triblock PAMAM-based nanocarriers for siRNA drug co-delivery. Biomaterials 2013, 34(4), 1289-1301. Rinkenauer, A C; Schallon, A.; Guenther, U.; Wagner, M.; Betthausen, E.; Schubert, U S; Schacher, F H, A Paradigm Change: Efficient Transfection of Human Leukemia Cells by Stimuli-Responsive Multicompartment Micelles. ACS Nano 2013, 7(11), 9621-9631 and EP 2 522 689 A1 and WO 2012/156058 A1.)

The disadvantage of this technical solution is that micellar systems are dynamic systems, which, below the critical micelle concentration, would mean a dissolution of the system into individual polymer strands, which is not expected for nanoparticles. A micelle dissolution or restructuring would be expected just upon the entry into organisms before the target organ or tissue is reached. The polymers used are also a triblock system, representing an increased production and characterization cost.

In addition, the complexation of the nucleic acids on the outer corona leads to increased risk of decomposition of the nucleic acid by nucleases despite complexation.

Furthermore, examples of micellization by inclusion of nucleic acids in the inner hydrophilic core of nanocarriers are known.

Here, a complexation of the nucleic acids with cationic, hydrophilic portions of block copolymers is carried out. The formulation method used here is intensive stirring of the components used (Osawa, S. Osada, K., Hiki, S., Dirisala, A., Ishii, T., Kataoka, K., Polyplex Micelles with Double-Protective Compartments of Hydrophilic Shell and Thermo-switchable Palisade of Poly(oxazoline)-Based Block Copolymers for Promoted Gene Transfection. Biomacromolecules 2016, 17(1), 354-361; Feng, G.; Chen, H.; Li, J.; Huang, Q.; Gupte, M J; Liu, H.; Song, Y.; Ge, Z., Gene therapy for nucleus pulposus regeneration by heme oxygenase-1 plasmid DNA carried by mixed polyplex micelles with thermo-responsive heterogeneous coronas. Biomaterials 2015, 52, 1-13).

The disadvantage of this technical solution is that the use of block copolymers leads an increased cost in the production and only a liquid storage is possible. In addition, the micellar systems show the same disadvantages which have already been mentioned above. The micellar tube systems mentioned also require a combination and thus the use of multiple block copolymers in the production.

With regard to the inclusion of nucleic acids in a hydrophobic polymeric system, the following technical solutions should be mentioned, for example:

By using nucleic acid formulations in nanoparticulate carrier systems consisting of cationic-hydrophilic and hydrophobic components, a high transfection efficiency can be achieved.

In this case, polymeric enveloping substances, homopolymers and block copolymers with amphiphilic character, and lipids are used. In the process, formulations with low cytotoxicity are used. The particles thus produced show high transfection efficiencies, high stability, or preferred solubilities of the polyplexes. (A nonviral pHEMA+chitosan nanosphere-mediated high-efficiency gene delivery system, Eroglu, Erdal; Tiwari, Pooja M.; Waffo, Alain B. Miller, Michael E., Vig, Volume 2013: 8(1) Pages 1403-1415 DOI https://dx.doi.org/10.2147/IJN.S43168; Ko, YT; Bickel, U., Liposomes Encapsulated Polyethyleneimines/Oligonucleotides Polyplexes Prepared by Reverse-Phase Evaporation Technique. Pharm. Sci. Tech 2012, 13(2), 373-378. Ge, X.;

Duan, S.; Wu, F.; Feng, J.; Zhu, H.; Jin, T., Polywraplex, Functionalized Polyplexes by Post-Polyplexing Assembly of a Rationally Designed Triblock Copolymer Membrane. Adv. Funct. Mater. 2015, 25(27), 4352-4363).

The disadvantage of these technical solutions is that, on the one hand, through the use of chitosan particles, an increased effort is necessary for the purification and presentation of the base particles. In addition, the use of ceric ammonium nitrate, which is also used to etch chromium, does not appear to be particularly suitable and also shows marked cytotoxicity in the particle combination at higher concentrations. Storage as a stable particle is also excluded in this case. The multicomponent carrier systems are produced using polyethylene glycol-lipid conjugates and block copolymers, and thus are also affected by the growing number of antibody-carrying organisms.

WO 2015035974 A1 discloses, for example, a nanostructured carrier system which comprises at least one polymer and/or at least one lipid and at least one polymethine dye, wherein the at least one polymethine dye acts as a targeting unit for the targeted transport of the nanostructured carrier system into a target tissue.

The disadvantage of this solution is that in this case a specific targeting is the goal and thus there is no accelerated endosomal release or active ingredient delivery. A use without the coloring properties of polymethine dyes is also much more pleasant for the end user. Another disadvantage is the limited interaction of polyethyleneimine with membranes.

In addition, protein dimers and lipid structures could be shown to be complexing agents for the nanoparticulate core.

Even in these cases, low toxicity and high transfections were visible. (Choi, K.-m.; Jang, M.; Kim, J H; Ahn, H J, Tumor-specific delivery of siRNA using supramolecular assembly of hyaluronic acid nanoparticles and 2b RNA-binding protein/siRNA complexes. Biomaterials 2014, 35(25), 7121-7132.)

The disadvantage of this technical solution is the use of 2b protein, which is a protein from a virus infecting tomato plants. The use of these viral proteins always poses an irritability for the immune system. The production of the shell polymer by the additional conjugation with cholesterol and the associated targeting or shielding effect also represents a further processing step and thus leads to high production costs.

WO 2010142660 A1, for example, discloses a pharmaceutically active formulation in the form of microparticles of defined size comprising siRNA, a highly hydrophobic biodegradable polymer and a cationic lipid which functions both as an amphipathic emulsifier and as a siRNA binding moiety, the siRNA and the cationic lipid are encapsulated within the microparticle.

The disadvantage of this technical solution is that use of microparticles can cause a difficult uptake in cell tissue. These are preferably taken up by immune cells and degraded, which should normally be prevented. In addition, the use of lipids in the formulation sometimes entails difficult large-scale production. The particles are therefore also intended for pulmonary uptake, that is to say the intake via the respiratory tract, and here too do not depend on a time-determined uptake.

In summary, the disadvantages of the technical solutions according to the prior art can be stated as follows:

The known carrier systems for the transport of nucleic acids as a whole show good transfection properties.

However, these carrier systems have the serious disadvantage that the nucleic acids to be transported complex on the particle-forming shell polymer of the carrier system or that the nucleic acids are present in uncomplexed form in the carrier system/particles.

Another disadvantage is that frequently no interaction with the genetic material takes place prior to micelle or particle formation.

In addition, the preparation processes for the carrier systems according to the prior art have the disadvantage that, in the preparation by means of stirring in solution, the micelle formation takes place by means of stirring in solution or dropwise addition in solution and the two-fold emulsion process (hydrophilic/hydrophobic/hydrophilic) are used so that no inclusion process with prior complexation of the active ingredient and subsequent nanoprecipitation of two solutions is possible.

Furthermore, the polymers and polymer-lipid derivatives known from the prior art have one or more hydrophobic subsections and one or more hydrophilic subsections so that these polymers or derivatives require a more elaborate preparation to produce nanoscale carrier systems.

SUMMARY OF THE INVENTION

The object of the present invention is to provide a nanostructured active ingredient carrier system which avoids the disadvantages of the prior art mentioned above and in particular allows a reduction of cytotoxic properties due to the formulation via the transport route.

In addition, the nano-structured active ingredient delivery system to be provided will allow interactions with cell membranes during the transport of hydrophilic components and, associated therewith, the generation of early endosomal release of the interaction complex from the carrier system.

Furthermore, a pharmaceutical composition is to be specified, containing a nanostructured active ingredient carrier system according to the invention as well as suitable auxiliaries and additives.

This object according to the invention is achieved by the characterizing features of the first patent claim. Further favorable embodiments of the invention are specified in the dependent claims.

BRIEF DESCRIPTION OF THE DRAWINGS

The present disclosure may be better understood, and its numerous features and advantages made apparent to those skilled in the art by referencing the accompanying drawings.

DETAILED DESCRIPTION

Figures 1, 2:
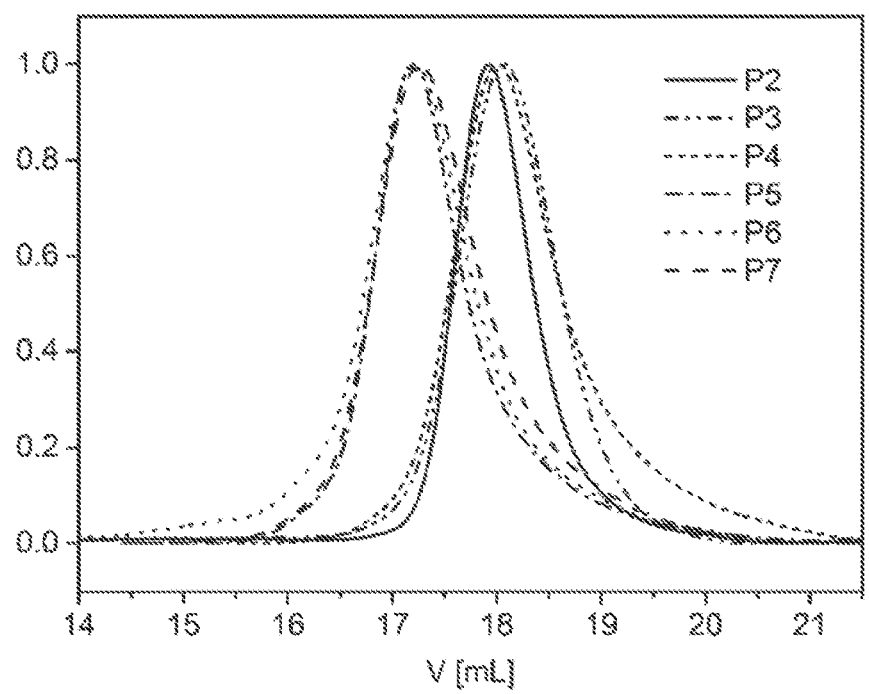
FIG. 1 includes a table showing the molecular weights and polydispersities of Boc-protected polymers according to embodiments.
FIG. 2 includes a graph showing the elution diagram of the size exclusion chromatography of the Boc-protected polymers taken by means of refractive index detection according to embodiments.

In the present disclosure, the terms below are to be understood as follows:

Nanoparticles are structures that are smaller than 1 µm and can be composed of multiple molecules. They are generally characterized by a higher surface to volume ratio and thus offer a higher chemical reactivity. These nanoparticles can consist of polymers.

Polymers are characterized by the repetition of certain units (monomers), but can also consist of several different repeat units. The monomers are covalently bonded together by the chemical reaction (polymerization) and form from the linking polymerizable unit. the so-called polymer backbone. The unconnected groups form the side chains where functional groups can be located. If these polymers have hydrophobic properties to some extent, they can form nanoscale structures (e.g., nanoparticles, micelles, vesicles) in an aqueous environment. "Shell polymer" is understood to mean one or more different polymers present in layers or as a blend wherein a random mixture of two or more polymers results in the formation of a hydrophobic nanostructured active ingredient carrier system, with an interaction complex is included and/or incorporated therein.

"Interaction complex" is understood to mean a complex formed by electrostatic interaction of one or more hydrophilic active ingredients and one or more complexing polymers.

"Active ingredient" describes at least one pharmaceutically active ingredient selected from the group, consisting of low molecular weight substances, inhibitors, inducers, or contrast agents, and in particular also of higher molecular weight substances, for example, in the form of nucleic acid, wherein the hydrophilic agents contain potentially therapeutically useful nucleic acids (e.g., short interferin RNA, short hairpin RNA, microRNA, plasmid DNA) and proteins (e.g., antibodies, interferons, cytokines).

The term "pharmaceutical active ingredient" is understood to mean any inorganic or organic molecule, substance or compound that has a pharmacological effect. The term "pharmaceutical active ingredient" is used synonymously herein with the term "medicine" and "medicament."

The pharmaceutical active ingredient can be those which have little or no bioavailability without inclusion in a nanoparticle or a liposome or have little or no stability in vivo.

The essence of the invention consists in providing a nanostructured active ingredient carrier system in the form of a shell polymer-enclosed, highly reactive nucleic acid-polymer complex, inter alia, for gene delivery.

This nano-structured active ingredient delivery system in the form of a particle consists of a carrier shell, wherein the carrier shell comprises at least one or more hydrophobic shell polymers, one or more charged complexing polymers, and one or more hydrophilic agents, wherein the complexing polymer interacts with the active ingredient.

The at least one shell polymer is selected from the group consisting of polyesters, poly(meth)acrylates, polystyrene derivatives, polyamides, polyurethanes, polyacrylonitriles, polytetrafluoroethylenes, silicones, polyethylene glycols, polyethylene oxides, and polyoxazolines and the copolymers thereof in various compositions, e.g., random, gradient, alternating, block, graft, or star copolymers.

Preferably, the at least one shell polymer is a biocompatible polymer.

The at least one shell polymer is particularly preferably a hydrophobic, biodegradable polymer, particularly preferably selected from the group consisting of PLGA, PLA, PCL, PGA, PEG, or PDX.

The "complexing polymer" represents one or more hydrophilic polymers which, through electrostatic interaction, are able to produce an interaction complex with one or more hydrophilic active ingredients.

More preferably, the complexing polymer consists of linear, water-soluble, cationic polymers with a proportion of 0 to 70% secondary amine functionalities in the polymer backbone. This at least one complexing polymer is selected from the group, consisting of polypeptides, poly(meth)acrylates, polystyrene derivatives, polyamides, polyurethanes, polyacrylonitriles, polyethylene glycols, polyethylene oxides, and polyoxazolines and their copolymers in various compositions, e.g., statistical, gradient, alternating, block, and graft copolymers. The invention expressly excludes the use of polyethyleneimine.

After incorporation of the nanostructured active ingredient carrier system (=nanoparticles) into the target tissue, there is the release of the interaction complex and an optionally included pharmaceutically active ingredient.

The release of a nanoparticle as part of the nanostructured active ingredient carrier system takes place as follows:
1. Acidification of the endosome, destabilization of the nano-structured carrier system, degradation of the shell polymer of the carrier shell by pH-dependent or enzymatic cleavage;
2. Release of the active interaction complex from the carrier shell, thereby allowing the complexing polymer to penetrate the endosome, the vesicular membrane;
3. Release of the active ingredient from the endosome. In this case, the active ingredient can already be unbound or else bound to complexing polymer; final release of the active ingredient follows
4. Polymer components are supplied to various metabolic pathways The advantage of this nanostructured active ingredient carrier system is that it allows a reduction in cytotoxic properties, the interactions with cell membranes during transport of hydrophilic components, and thus the generation of early endosomal release of the interaction complex from the carrier system, resulting in optimal active ingredient release.

Another object of the present invention relates to a pharmaceutical composition comprising such a nanostructured active ingredient carrier system as well as suitable auxiliaries and additives.

The term "auxiliaries and additives" according to the invention means any pharmacologically acceptable and therapeutically meaningful substance which is not a pharmaceutical active ingredient but can be formulated together with the pharmaceutical active ingredient in the pharmaceutical composition to influence, in particular to improve, qualitative properties of the pharmaceutical composition.

Preferably, the auxiliaries and/or additives do not develop any significant or at least no undesirable pharmacological effect with regard to the intended treatment.

Suitable auxiliaries and additives are, for example, pharmaceutically acceptable inorganic or organic acids, bases, salts, and/or buffer substances. Examples of inorganic acids are hydrochloric acid, hydrobromic acid, nitric acid, sulfuric acid, and phosphoric acid, with hydrochloric acid and sulfuric acid in particular being preferred.

Examples of suitable organic acids are malic acid, tartaric acid, maleic acid, succinic acid, acetic acid, formic acid, and propionic acid, and particularly preferably ascorbic acid, fumaric acid, and citric acid. Examples of pharmaceutically acceptable bases are alkali hydroxides, alkali metal carbonates, and alkali ions, preferably sodium. Mixtures of these substances can be used in particular for adjusting and buffering the pH value.

Preferred buffer substances are furthermore PBS, HEPES, TRIS, MOPS, and other physiologically acceptable buffer substances.

Further suitable auxiliaries and additives are solvents or diluents, stabilizers, suspension agents, preservatives, fillers, cryoprotectants, emulsion mediators and/or binders, and other conventional auxiliaries and additives known in the art. The choice of auxiliaries and the amounts thereof to be used will depend on the pharmaceutical active ingredient and the mode of administration.

A nanostructured active ingredient carrier system, which forms the pharmaceutical composition with the suitable auxiliaries and additives, can be achieved, for example, by the double emulsion method known per se.

The nanostructured active ingredient carrier system and the pharmaceutical composition, which comprises such a nanostructured active ingredient carrier system and suitable auxiliaries and additives, represent a hitherto unique, combinable therapeutic systems to transport a variety of substances, especially pharmaceutical active ingredients (e.g., nucleic acids, but also hydrophilic molecules) into a cell, wherein the combination with the interaction complex leads to an early endosomal release. The safe transport into the cell is realized by the shell protein and the interaction complex. The result is a fast endosomal release, which is ensured by the interaction of the interaction complex with the endosomal membrane. In this way, it is possible to efficiently and rapidly introduce and release one or more active ingredients into cells.

Figure 3:
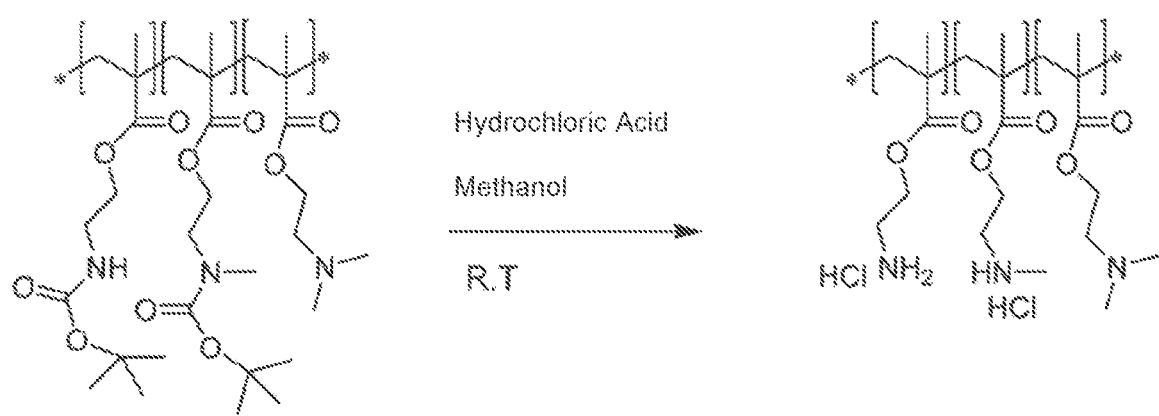
FIG. 3 includes the reaction scheme of the complexing polymer preparation according to one embodiment.
Figure 4:
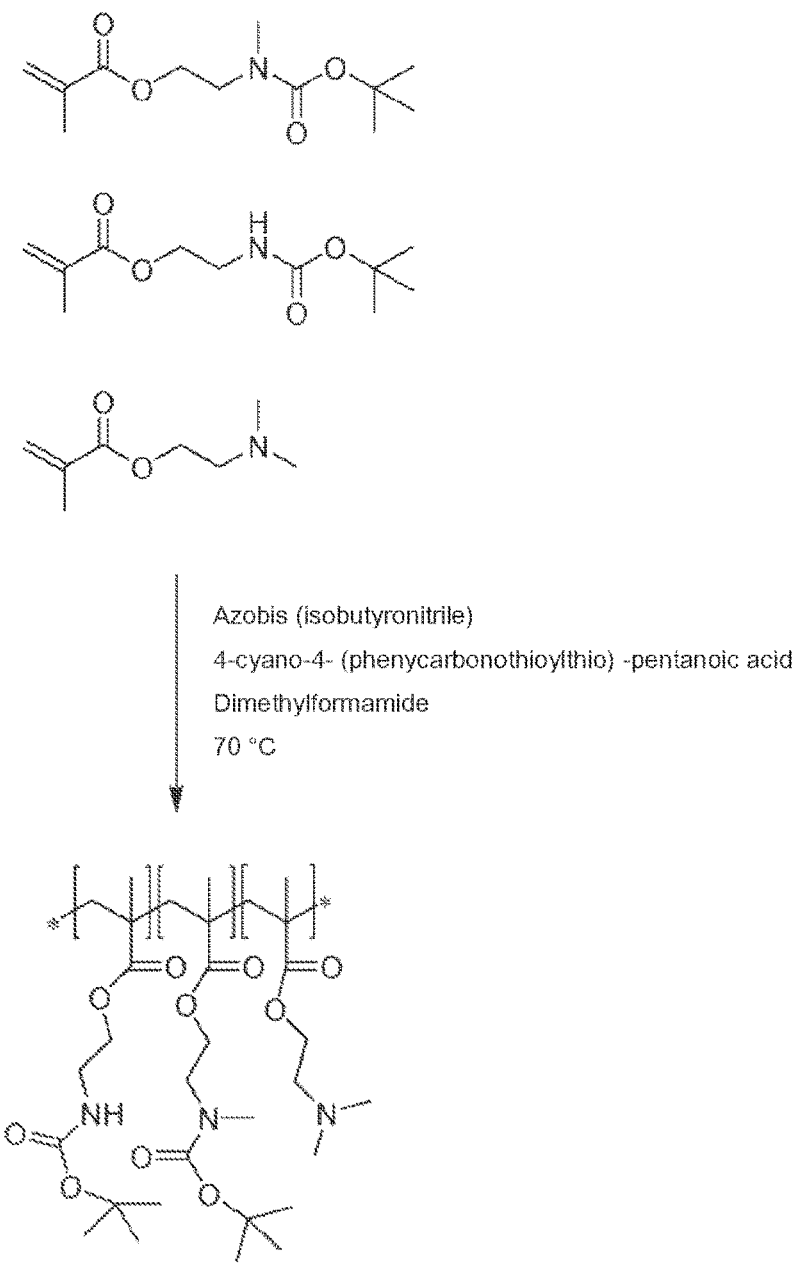
FIG. 4 includes the reaction scheme of the cleavage reaction of the Boc group according to one embodiment.
Figure 5:
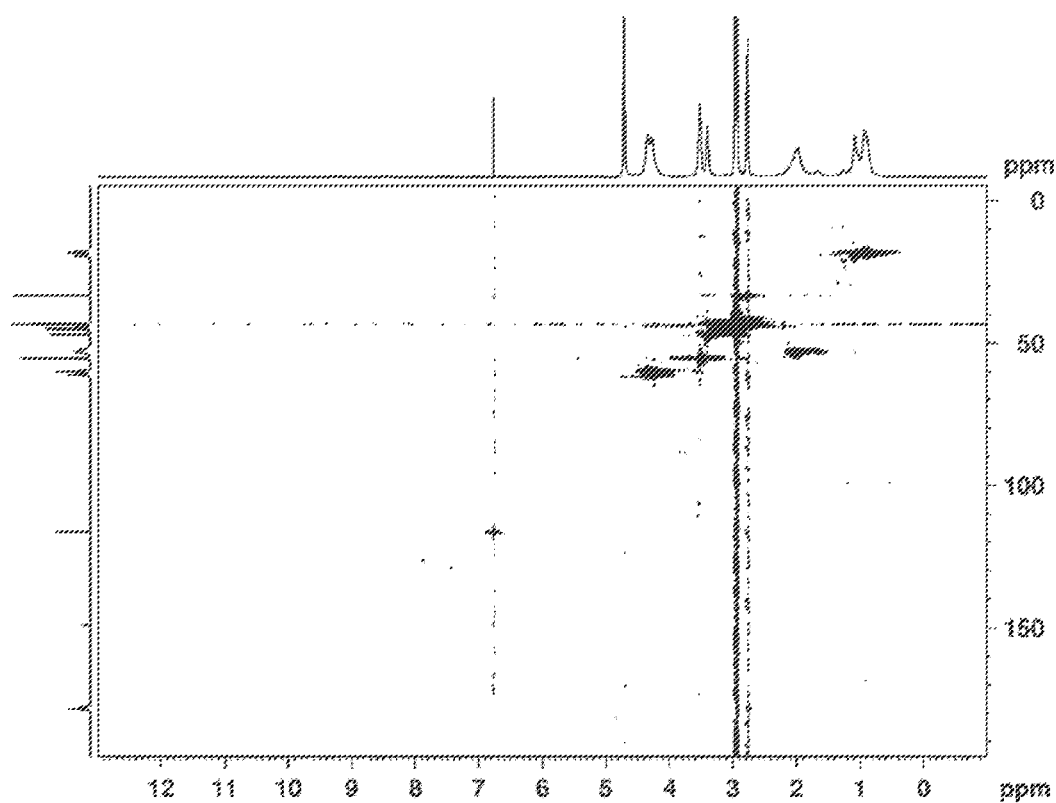
FIG. 5 includes a graph illustrating the 2-D HSQC-NMR of the cleavage reaction of the Boc group according to one embodiment.
Figure 6:
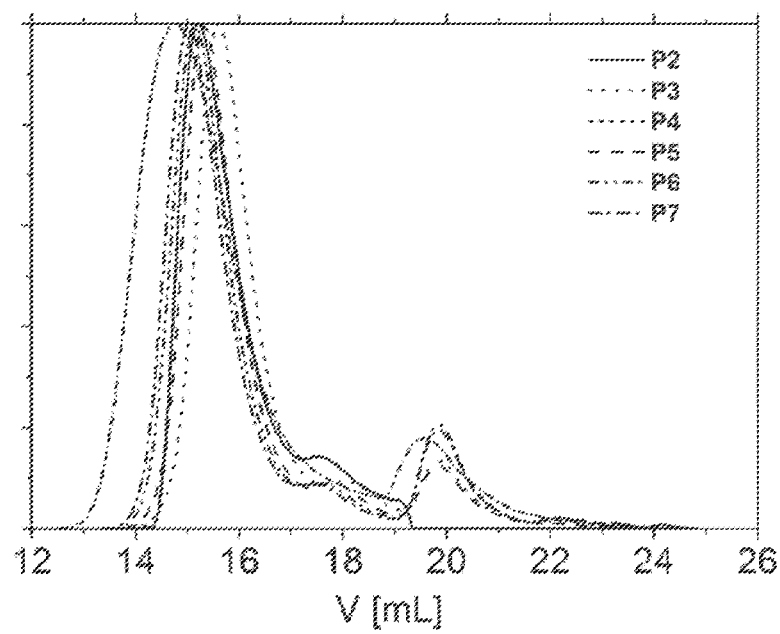
FIG. 6 includes a graph showing the elution diagram of the size exclusion chromatography of the complexing polymers recorded by means of refractive index detection.
Figures 7, 8:
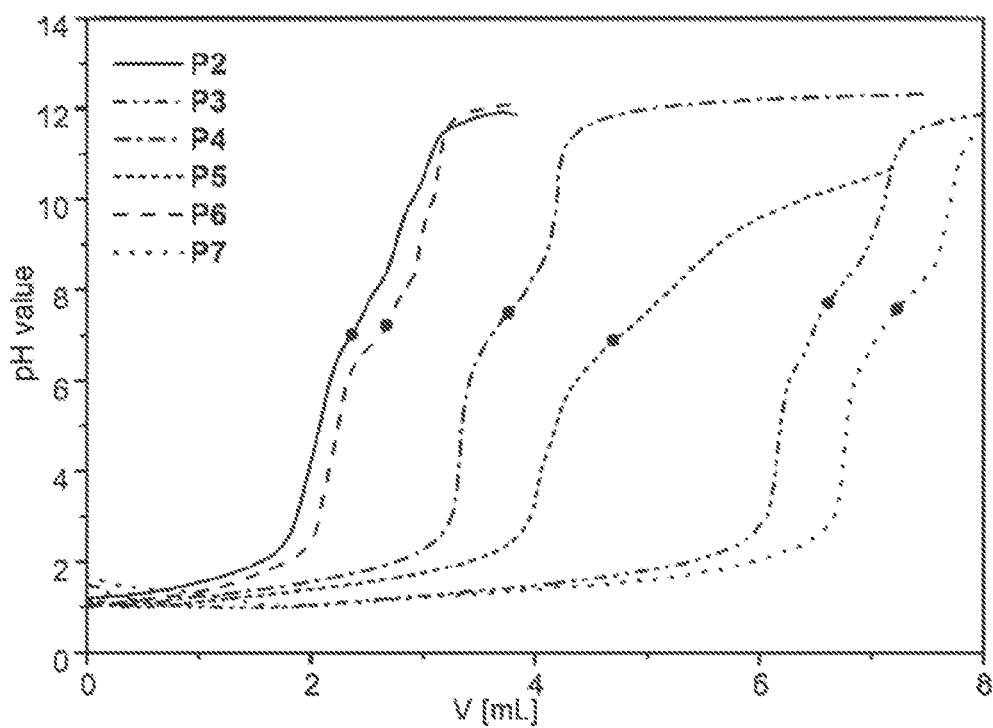
FIG. 7 includes a table showing the molecular weights and polydispersities of the Boc-protected polymers determined by a) AF4 by means of MALS detection, b) and c) by SEC (0.1% TFA, 0.1M NaCl dextran calibration/c DmAc, 0.21% LiCl, PMMA calibration), and d) the degree of polymerization determined by AF4 and $^1$H NMR spectroscopy according to embodiments.
FIG. 8 includes a graph showing the titration curves of the complexing polymers 2 to 7 in a diagram vs. the total volume of the titrant used, according to embodiments.

The invention will be explained in more detail below with reference to the figures and the exemplary embodiments. In the figures:

FIG. 1: shows the molecular weights and polydispersities of the Boc-protected polymers determined by a) SEC (DmAc, 0.21% LiCl, PMMA calibration), and b) the degree of polymerization determined by means of SEC and $^1$H-NMR spectroscopy, FIG. 2: shows the elution diagram of the size exclusion chromatography of the Boc-protected polymers taken by means of refractive index detection, FIG. 3: shows the reaction scheme of the complexing polymer preparation according to exemplary embodiment 1, FIG. 4: shows the reaction scheme of the cleavage reaction of the Boc group according to exemplary embodiment 2, FIG. 5: shows the 2-D HSQC-NMR of the cleavage reaction of the Boc group according to exemplary embodiment 2, FIG. 6: shows the elution diagram of the size exclusion chromatography of the complexing polymers recorded by means of refractive index detection, FIG. 7: shows the molecular weights and polydispersities of the Boc-protected polymers determined by a) AF4 by means of MALS detection, b) and c) by SEC (0.1% TFA, 0.1M NaCl dextran calibration/c DmAc, 0.21% LiCl, PMMA calibration), and d) the degree of polymerization determined by AF4 and $^1$H NMR spectroscopy. In addition, the pKA value of the polymers was determined by titration, FIG. 8: shows the titration curves of the complexing polymers 2 to 7 in a diagram vs. the total volume of the titrant used, FIG. 9: shows the superimposition of the $^1$H-NMR spectra A) copolymer of the complexing polymers with Boc group, B) complexing polymer after elimination reaction with hydrochloric acid, C) complexing polymer after the cleavage reaction with trifluoroacetic acid, FIG. 10: shows the reaction scheme of the NHS ester coupling reaction, FIG. 11A: shows the size of the particles produced directly after the preparation and removal of the solvent and after freeze-drying and resuspension in ultrapure water, FIG. 11B: shows the polydispersity of the particles produced directly after preparation and removal of the solvent and after freeze-drying and resuspension in ultrapure water, FIG. 11C: shows the zeta potential of the particles produced directly after the preparation and removal of the solvent and after freeze-drying and resuspension in ultrapure water.

Figure 12A:
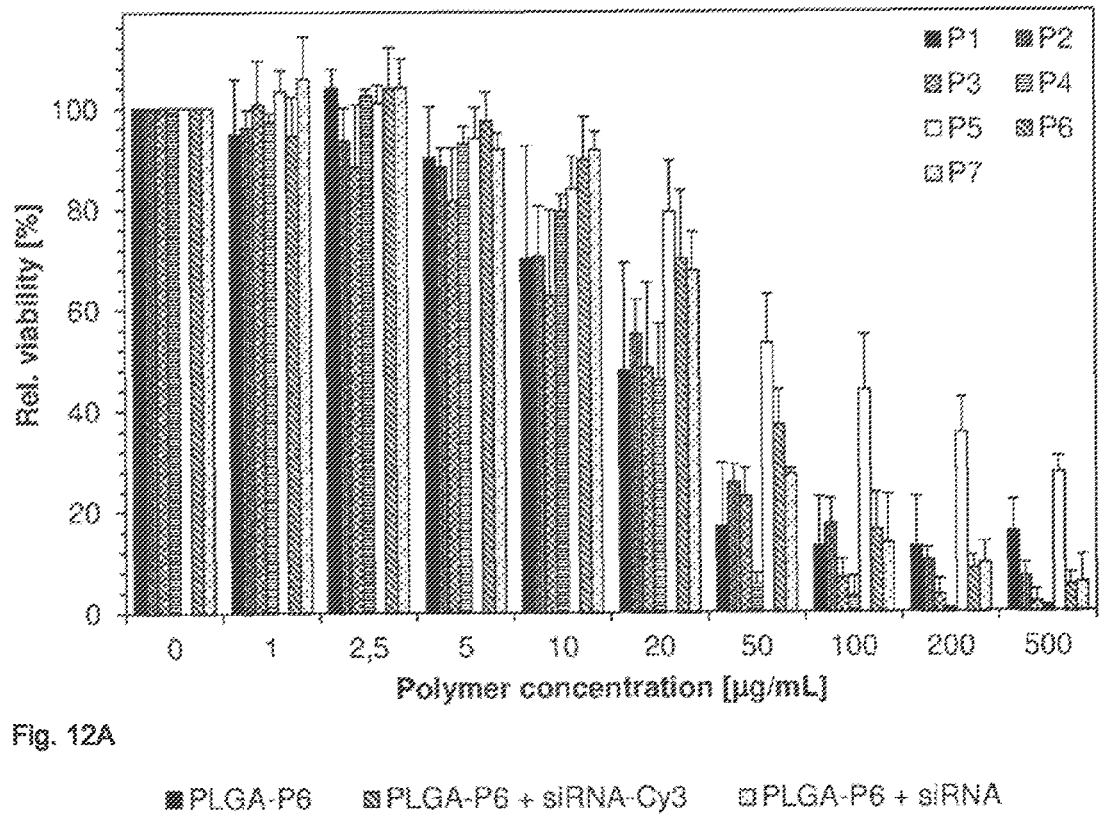
FIG. 12A includes a graph showing the relative viability of L929 fibroblast cells, 24 h after the addition of interaction complexes, according to embodiments.
Figure 12B:
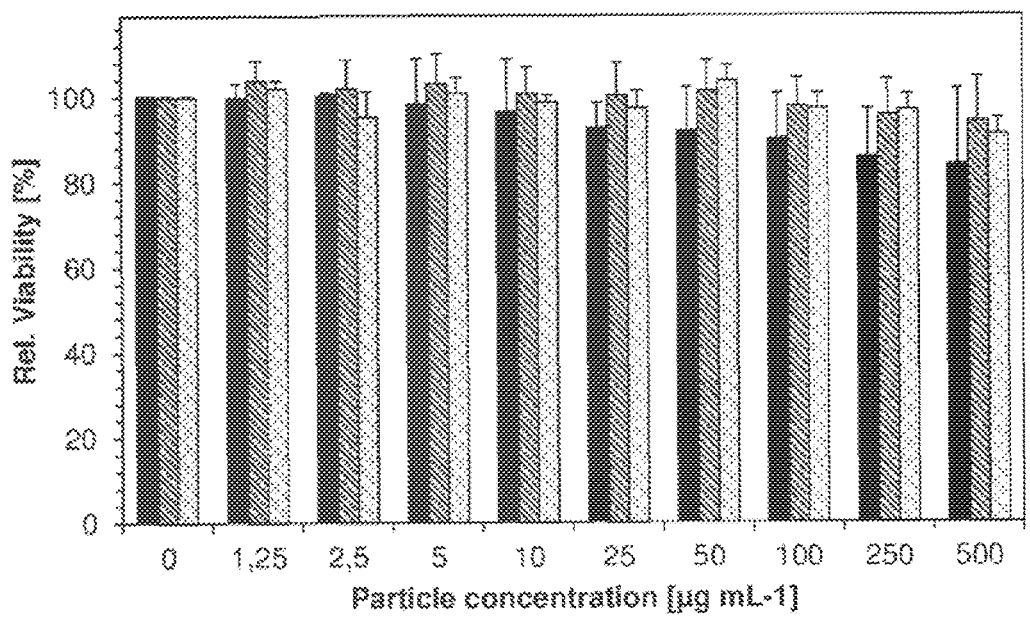
FIG. 12B includes a graph showing the relative viability of L929 fibroblast cells, 24 h after the addition of nanoparticles (B) in the corresponding concentrations, according to embodiments.
Figure 13:
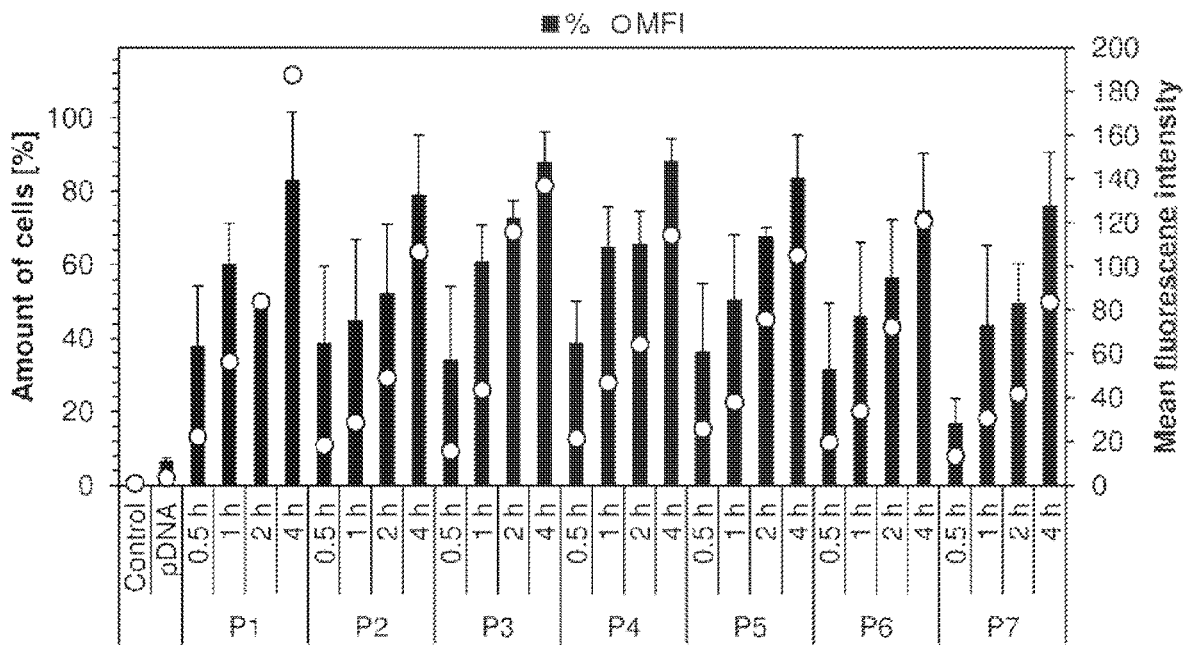
FIG. 13 includes a graph showing the time-dependent uptake of the interaction complexes P1 to P6 in HEK cells according to embodiments.
Figure 14:
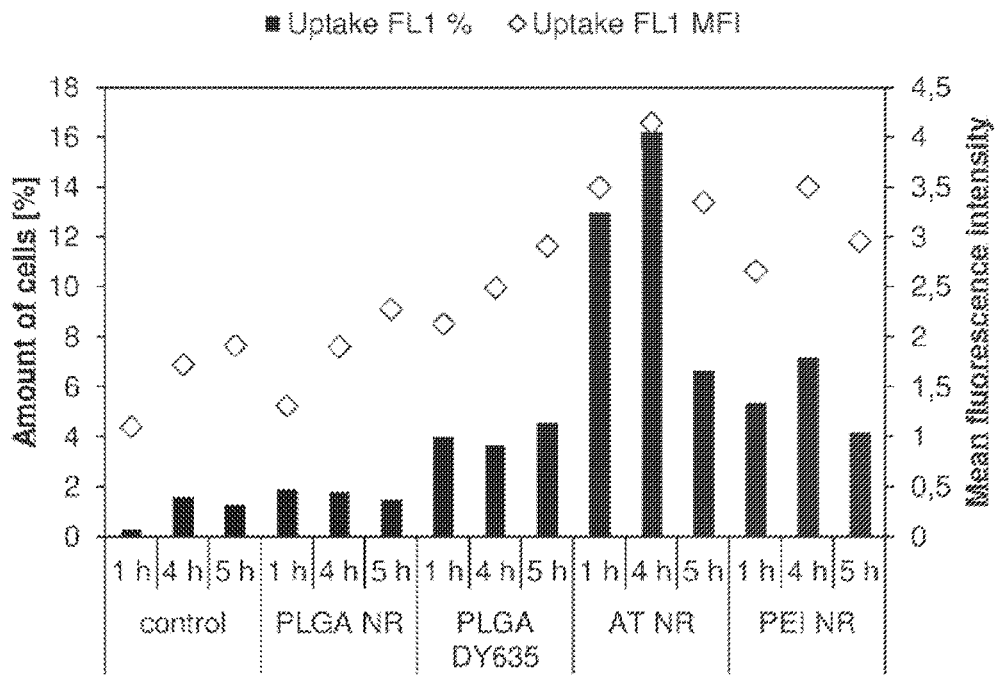
FIG. 14 includes a graph showing the time-dependent uptake of P6 and siRNA encapsulated nanoparticles in HEK cells compared to PEI nanoparticles according to embodiments.
Figure 15:
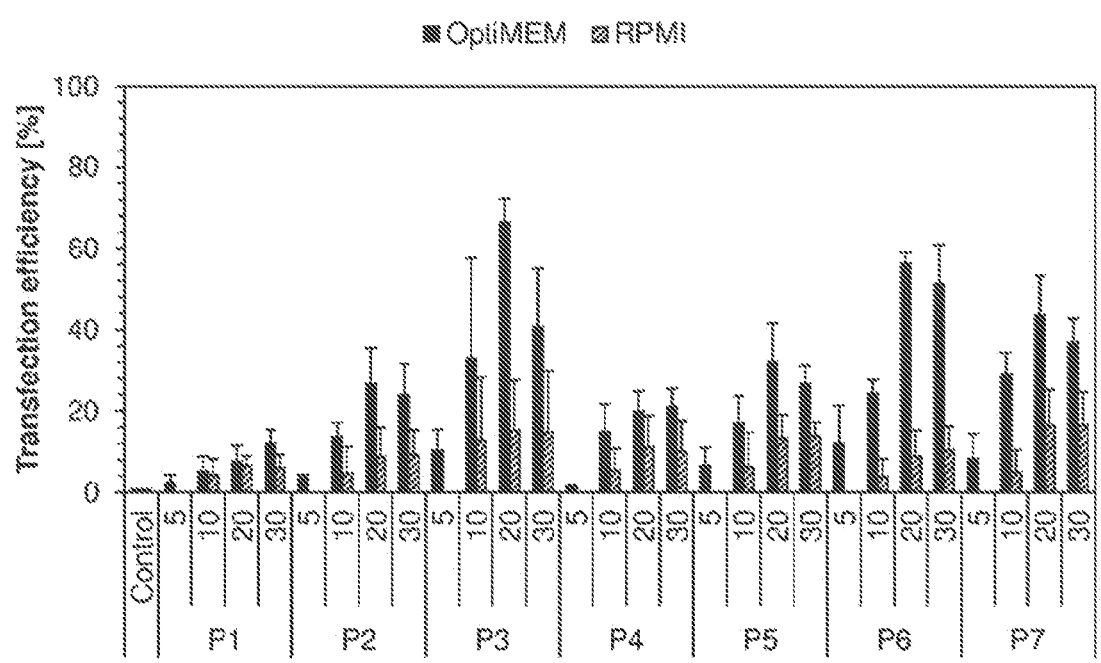
FIG. 15 includes a graph showing the transfection efficiency of the interaction polyplexes with GFP-coded pDNA in HEK cells under the influence of serum-reduced medium (OptiMEM) and serum-containing standard growth medium (RPMI) according to embodiments.

FIG. 12A: shows the relative viability of L929 fibroblast cells, 24 h after the addition of interaction complexes, FIG. 12B: shows the relative viability of L929 fibroblast cells, 24 h after the addition of nanoparticles (B) in the corresponding concentrations, FIG. 13: shows the time-dependent uptake of the interaction complexes P1 to P6 in HEK cells, FIG. 14: shows the time-dependent uptake of P6 and siRNA encapsulated nanoparticles in HEK cells compared to PEI nanoparticles, and FIG. 15: shows the transfection efficiency of the interaction polyplexes with GFP-coded pDNA in HEK cells under the influence of serum-reduced medium (OptiMEM) and serum-containing standard growth medium (RPMI).

EXAMPLES

Exemplary Embodiment 1

Synthesis of Complexing Polymers

Homo- and copolymers of N-tert-butyloxycarbonyl-(2-aminoethyl) methacrylates (hereinafter BocAEMA), N-methyl-N-tert-butyloxycarbonyl-(2-aminoethyl) methacrylates (hereinafter BocMAEMA) and N,N-dimethyl-(2-aminoethyl) methacrylates (hereinafter DMAEMA) were prepared by reversible addition-fragmentation chain transfer polymerization.

In a typical reaction, 0.73 g of BocAEMA ($3.18 \times 10^{-3}$ mol), 0.77 g of BocMAEMA ($3.18 \times 10^{-3}$ mol), 0.98 mg of azobis(isobutyronitrile) initiator ($5.96 \times 10^{-5}$ mol), 5.68 mg of 4-cyano-4-(phenylcarbonothioylthio)pentanoic acid ($20.33 \times 10^{-5}$ mol), and 5.03 mL of dimethylformamide were added together with anisole as internal standard (0.34 mL) in a 25 mL microwave reaction vessel, and this was degassed for 30 min using an argon stream.

The reaction solution was then heated with stirring in an oil bath, preheated to 70° C., for 38 h.

The copolymer was precipitated twice from tetrahydrofuran in n-hexane and then dried under reduced pressure.

The conversion was determined using the $^1$H-NMR spectrum against the internal standard.

The analytical data are shown in FIG. 1, the size exclusion chromatography is shown in FIG. 2, and the synthetic scheme is shown in FIG. 4.

The tert-butyloxycarbonyl (Boc) protected polymers were deprotected in 1M methanolic hydrochloric acid over 16 h, the solvent removed under reduced pressure, dissolved in deionized water, and lyophilized for 24 h.

Figure 9:
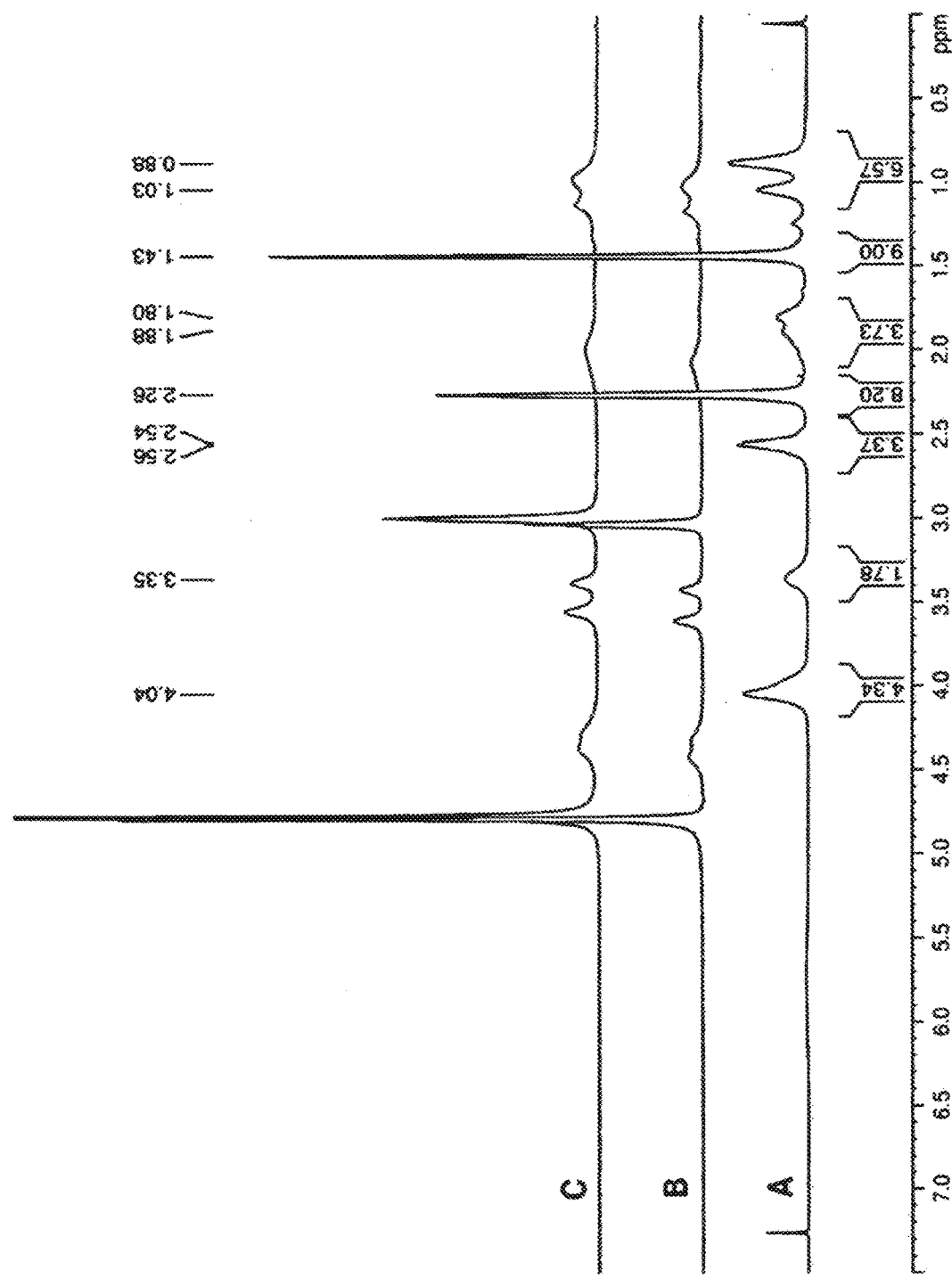
FIG. 9 includes a graph showing the superimposition of the $^1$H-NMR spectra A) copolymer of the complexing polymers with Boc group, B) complexing polymer after elimination reaction with hydrochloric acid, C) complexing polymer after the cleavage reaction with trifluoroacetic acid, according to embodiments.

The synthetic scheme is shown in FIG. 3, the 2-D NMR is shown in FIG. 5, the size exclusion chromatography is shown in FIG. 6, the analytical data is shown in FIG. 7, the titration curves with the $pK_A$ values are shown in FIG. 8, and the $^1$H-NMR comparison of deprotection methods is shown in FIG. 9.

Exemplary Embodiment 2

Functionalization of Complexing Polymers and Shell Polymers

The linkage of the polymers to fluorescent dyes by means of N-hydroxysuccinimide (hereinafter, NHS) activated coupling of carboxylic acids with primary amines was used for the visualization of the shell and complexing polymers.

For this purpose, in a typical reaction, the NHS-ester derivative of cyanine 5® (0.5 mg, $8.1 \times 10^{-4}$ mol) (together with the copolymer PMAEMA-co-AEMA 37.0 mg, $6.8 \times 10^{-4}$ mol) and triethylamine (0.3 mL) were stirred in methanol (9.7 mL) for 24 h at room temperature under the exclusion of light. The solvent was then removed under reduced pressure, the solid residue dissolved in water and dialyzed against distilled water for 7 days in a regenerated cellulose dialysis membrane tube (Carl Roth, exclusion limit 3500 g·mol$^{-1}$), and then freeze-dried for 24 h.

Figure 10:
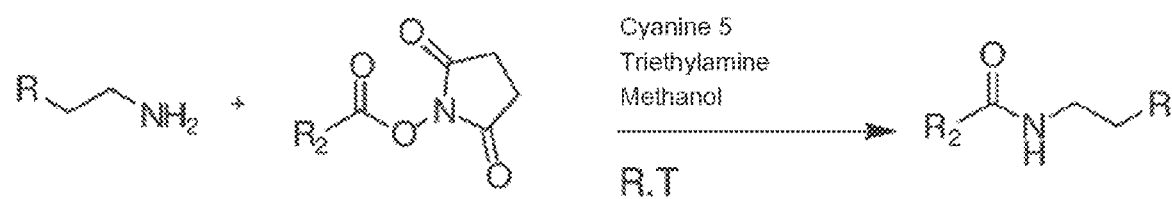
FIG. 10 includes a graph showing the reaction scheme of the NHS ester coupling reaction according to one embodiment.

The synthetic scheme is shown in FIG. 10.

Exemplary Embodiment 3

Production of Nanoparticles

The particles used are prepared, for example, by means of double emulsion. High-frequency ultrasound is used, which favors the formation of nanoscale particles with the aid of the surface-active substance polyvinyl alcohol (PVA).

For this purpose, the hydrophobic shell polymers are dissolved in ethyl acetate, a water-immiscible solvent (10-20 mg·mL$^{-1}$).

A final concentration of 0.3% PVA in ultrapure water is used.

The interaction complex is previously formed from the complexing polymer and the genetic material, here the siRNA, in ultrapure water. Subsequently, a first emulsion of interaction complex and shell polymer is formed, which is subsequently transferred to water and, after reapplication of high-frequency ultrasound, a second emulsion is formed.

Subsequently, the particles are incubated for up to 48 h at room temperature to allow the organic solvent to evaporate.

The particles formed are washed by centrifugation and resuspension in ultrapure water, treated with 5% sucrose, and then frozen (−80° C.) to be lyophilized.

Exemplary Embodiment 4

Characterization of the Nanoparticles

Nanoparticles of PLGA, polymethacrylates and siRNA are reproducibly produced with constant parameters.

Figure 11A:
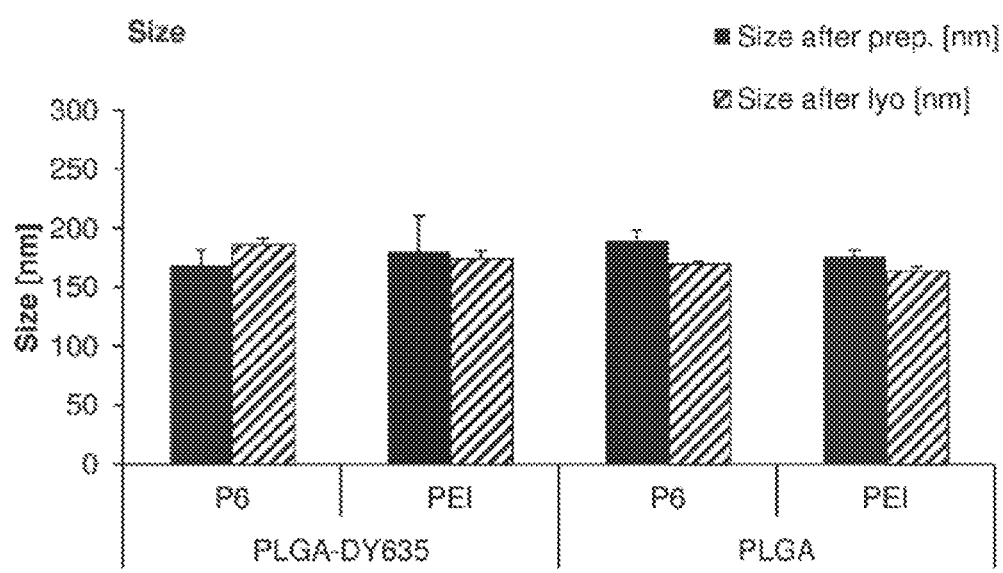
FIG. 11A includes a graph showing the size of the particles produced directly after the preparation and removal of the solvent and after freeze-drying and resuspension in ultrapure water according to embodiments.
Figure 11B:
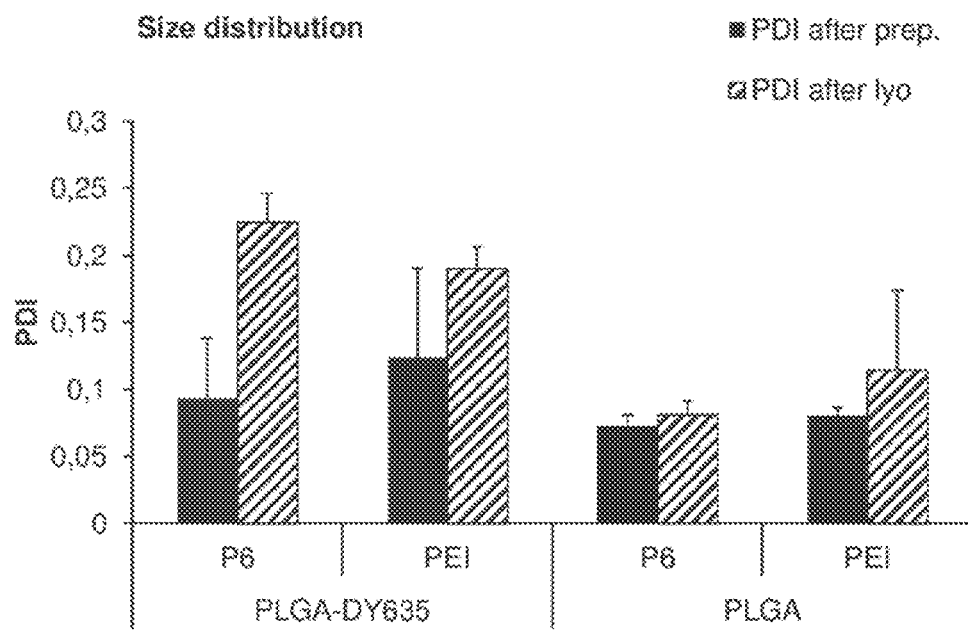
FIG. 11B includes a graph showing the polydispersity of the particles produced directly after preparation and removal of the solvent and after freeze-drying and resuspension in ultrapure water according to embodiments.
Figure 11C:
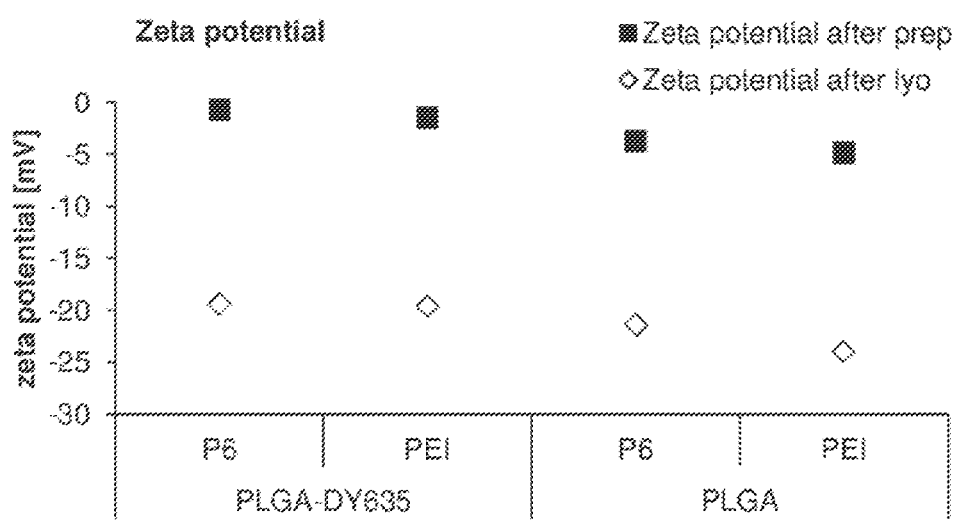
FIG. 11C includes a graph showing the zeta potential of the particles produced directly after the preparation and removal of the solvent and after freeze-drying and resuspension in ultrapure water, according to embodiments.

The results are shown in FIGS. 11A to 11C, where A=size, B=polydispersity, C=zeta potential surface charge. For the size and size distribution measurement, dynamic light scattering is used; the charge is determined by ζ-potential.

FIG. 11A shows that the size of the particles remains constant regardless of the preparation or the shell or complexing polymer used.

Exemplary Embodiment 5

Toxicity of Interaction Complex and Nanoparticles

The cytotoxicity studies is carried out according to the ISO10993-5 protocol with L929 mouse fibroblast cells. The cells are seeded in DMEM growth medium (Dulbecco's modified Eagle's medium) at a cell concentration of $10^4$ cells per well in a 96-well plate, and were incubated for 24 h at 37° C. and 5% $CO_2$.

This is followed by the addition of the corresponding complexes or nanoparticles in various concentrations.

After 24 h, the medium is exchanged with fresh medium, treated with the reagent AlamarBlue.

After a further incubation period of 4 h at 37° C., the fluorescence measurement of the individual wells was carried out using a microplate reader (Tecan) at an excitation wavelength of 570 nm and an emission wavelength of 610 nm. Untreated cells served as a negative control, with their measurements corresponding to a viability of 100%. The results are shown in FIGS. 12A and 12B. It can be clearly seen that encapsulation led to an increase in biocompatibility.

Exemplary Embodiment 6

Cellular Uptake of Interaction Complex and Nanoparticles

To study the cellular uptake of complexes and nanoparticles, human embryonic kidney cells (HEK) are seeded into 24-well plates in RPMI 1640 growth medium (containing 10% fetal calf serum and 1% antibiotic).

After 24 h, the medium is exchanged for serum-reduced medium (OptiMEM) and incubated for a further hour.

Polyplexes with YOYO-labeled pDNA or nanoparticles with Nile Red and complexing polymer is added to the HEK cells and incubated for up to 4 h at 37° C., 5% $CO_2$.

Cellular uptake is assessed by flow cytometry. A total of 10,000 cells is measured, and all living cells (FSC/SSC scattering) with a positive signal (FL1) are counted.

The results are shown in FIG. 13 and FIG. 14.

The investigation of the cellular particle uptake was performed via confocal laser scanning microscopy. For this purpose, HEK cells are seeded in microscopy vessels with a glass bottom and the microscopic uptake by the cells takes place 1 to 4 hours after addition of the samples. Furthermore, the cell nuclei are stained with Hoechst 33342, lysosomes with LysoTracker Red DND-99 or LysoTracker Green DND-26, and cell membranes with CellMask Orange plasma membrane stain.

Exemplary Embodiment 7

Transfection and Knockdown

For the transfection studies, HEK cells or a stable GFP-CHO cell line are seeded in 24-well plates with a cell concentration of $10^{15}$ cells/mL.

One hour before the addition of the samples, the medium is exchanged either with serum-reduced medium (OptiMEM) or serum-containing growth medium (RPMI 1640).

Polyplexes or nanoparticles are added to the cells (50 µL per well) and incubated for 4 h at 37° C., 5% $CO_2$.

Thereafter, the supernatant is removed and the cells are incubated in fresh growth medium for a further 24 h to 72 h.

The analysis of the transfection efficiency is carried out by flow cytometry. To this end, the cells are trypsinized and stained with propidium iodide for a live/dead determination.

To determine the transfection efficiency, 10,000 cells are measured and all living cells with positive GFP signal ($E_x$ 488 nm; $E_m$ 525 nm) are counted. The transfection results are shown in FIG. 15.

All features described in the description, the exemplary embodiments, and the following claims can be essential to the invention both individually and in any combination with one another.

What is claimed is:

1. A nanostructured active ingredient carrier system comprising at least one hydrophobic shell polymer, at least one complexing polymer, and at least one hydrophilic active ingredient, wherein the complexing polymer interacts with the active ingredient, and the complexing polymer comprises primary amino groups, secondary amino groups, or a combination of primary and secondary amino groups, and wherein the hydrophilic active ingredient includes a genetic material, or a peptide, or a protein; and the complexing polymer includes at least one of a polypeptide, a poly (methacrylate), a polystyrene, a polyamide, a polyacrylamide, a polyurethane, a polyacrylonitrile, a polyethylene glycol, a polyethylene oxide, a polyoxazoline, or any copolymer thereof.

2. The nanostructured active ingredient carrier system according to claim 1, wherein an interaction between the complexing polymer and the active ingredient is caused by one or more non-covalent interactions in the form of electrostatic bonds, ionic bonds, hydrogen bonds, or van der Waals forces.

3. The nanostructured active ingredient carrier system according to claim 1, wherein the genetic material includes siRNA, mRNA, ncRNA, saRNA, short hairpin- RNA, micro-RNA, or plasmid-DNA, or a combination thereof.

4. The nanostructured active ingredient carrier system according to claim 3, wherein the genetic material includes siRNA.

5. The nanostructured active ingredient carrier system according to claim 1, wherein the hydrophilic active ingredient includes antibodies, interferons, or cytokines.

6. The nanostructured active ingredient carrier system according to claim 1, wherein the complexing polymer includes poly-N,N-dimethyl-(2-aminoethyl) -methacrylate (PDMAEMA), poly-(2-aminoethyl)-methacrylate (PAEMA), poly-N-methyl-(2-amioethyl)-methacrylate (PMAEMA), or a copolymer thereof, or any combination thereof.

7. The nanostructured active ingredient carrier system according to claim 1, characterized in that the hydrophobic shell polymer includes at least one of a polyester, a poly (meth) acrylate, a polystyrene, a polyamide, a polyurethane, a polyacrylonitrile, a polytetrafluoroethylene, a silicone, a polyethylene glycol, a polyethylene oxide, a polyoxazoline, or any combination or copolymer thereof.

8. The nanostructured active ingredient carrier system according to claim 1, characterized in that the hydrophobic shell polymer is a biocompatible polymer.

9. The nanostructured active ingredient carrier system according to claim 1, further comprising sucrose, trehalose, or glucose.

10. The nanostructured active ingredient carrier system of claim 1, wherein the nanostructured active ingredient carrier system is free of polyethyleneimine.

11. The nanostructured active ingredient carrier system of claim 1, wherein the active ingredient carrier system is a nanoparticle having a size not greater than 1 micron.

12. The nanostructured active ingredient carrier system of claim 1, wherein the complexing polymer comprises at least two types of amino groups, the two types of amino groups being selected from primary amino groups, secondary amino groups and tertiary amino groups.

13. The nanostructured active ingredient carrier system of claim 1, wherein the complexing polymer comprises primary amino groups and secondary amino groups.

14. The nanostructured active ingredient carrier system of claim 1, wherein the complexing polymer comprises primary amino groups, secondary amino groups, and tertiary amino groups.

15. A nanostructured active ingredient carrier system comprising a shell polymer, the shell polymer including poly (lactic-co-glycolic acid) (PLGA);

a complexing polymer, the complexing polymer including a polymethacrylate; and a hydrophilic active ingredient, wherein the nanostructured active ingredient carrier system is free of a polymethine dye, and the hydrophilic active ingredient includes a genetic material, a peptide or a protein.

16. A nanostructured active ingredient carrier system comprising at least one hydrophobic shell polymer, at least one complexing polymer, and at least one hydrophilic active ingredient, wherein the complexing polymer interacts with the active ingredient, a transfection efficiency is at least 20%, and wherein the nanostructured active ingredient carrier system is free of a polymethine dye, and the hydrophilic active ingredient includes a genetic material, a peptide or a protein.

* * * * *